(12) United States Patent
Lofving et al.

(10) Patent No.: US 8,056,583 B2
(45) Date of Patent: Nov. 15, 2011

(54) SEALING MEANS, KIT AND METHOD FOR SEALING OF HOLLOW HOSES OF FLEXIBLE MATERIAL

(75) Inventors: Alf Lofving, Torslanda (SE); Jan Davidsson, Kode (SE); Anders Karlsson, Skepplanda (SE)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 12/462,545

(22) Filed: Aug. 5, 2009

(65) Prior Publication Data

US 2010/0282350 A1  Nov. 11, 2010

(30) Foreign Application Priority Data

May 11, 2009  (SE) ...................... 0900645

(51) Int. Cl.
*F16L 55/16* (2006.01)
(52) U.S. Cl. ............... 138/99; 138/97; 285/373; 285/15
(58) Field of Classification Search ............. 138/99, 138/97, 157, 162; 285/373, 15, 156
See application file for complete search history.

(56) References Cited

U.S. PATENT DOCUMENTS

| | | | | |
|---|---|---|---|---|
| 924,262 A * | 6/1909 | Moll | ...... | 138/99 |
| 1,445,858 A * | 2/1923 | Tallman | ...... | 138/99 |
| 1,721,864 A * | 7/1929 | Johnson | ...... | 138/99 |
| 2,408,253 A * | 9/1946 | Diebold | ...... | 174/136 |
| 3,689,114 A * | 9/1972 | Meserole | ...... | 285/373 |
| 3,771,820 A * | 11/1973 | Hoss et al. | ...... | 285/373 |
| 4,109,944 A * | 8/1978 | Curtin | ...... | 285/373 |
| 4,260,181 A * | 4/1981 | Curtin | ...... | 285/15 |
| 4,268,559 A * | 5/1981 | Smuckler | ...... | 428/99 |
| 4,448,824 A * | 5/1984 | Holmes et al. | ...... | 428/33 |
| 4,465,309 A * | 8/1984 | Nimke et al. | ...... | 285/373 |
| 4,673,122 A * | 6/1987 | Dubey | ...... | 228/119 |
| 5,007,666 A * | 4/1991 | Kyfes | ...... | 285/373 |
| 5,722,463 A * | 3/1998 | Smyth et al. | ...... | 138/170 |
| 6,779,575 B1 | 8/2004 | Arthun | ...... | 156/515 |
| 7,066,210 B2 * | 6/2006 | Kakoschke et al. | ...... | 138/99 |
| RE41,169 E | 3/2010 | Arthun | ...... | 156/515 |
| 2009/0250157 A1 | 10/2009 | Arthun | ...... | 156/198 |
| 2010/0185127 A1 | 7/2010 | Nilsson | ...... | 601/41 |

FOREIGN PATENT DOCUMENTS

| | | |
|---|---|---|
| EP | 1090281 B1 | 12/2005 |
| EP | 1650009 A2 | 4/2006 |
| EP | 1650009 A3 | 4/2008 |
| JP | 05280686 A * | 10/1993 |
| WO | 2010/008396 A2 | 1/2010 |

* cited by examiner

*Primary Examiner* — Patrick F Brinson

(57) ABSTRACT

The present invention relates to sealing means made of a plastically deformable material for mechanical sealing of hollow hoses (2) of elastic material by means of an appliance having at least two jaws, at least one of which is movable towards and away from the other and which, when moving towards each other, crimp the sealing means against the hose (2) for contamination-tight sealing of the same, the sealing means (20) comprises at least one sealing member (4, 4'; 44, 44'; 64, 64'; 74, 74'; 84), which has two opposite ends and an opening (40, 40') that extends between said ends to allow the at least one sealing member to be slipped onto the hose (2) to be sealed.

The present invention also relates to a kit comprising a sealing means and an appliance for sealing of hollow hoses and to a method for mechanical sealing of hollow hoses.

12 Claims, 5 Drawing Sheets

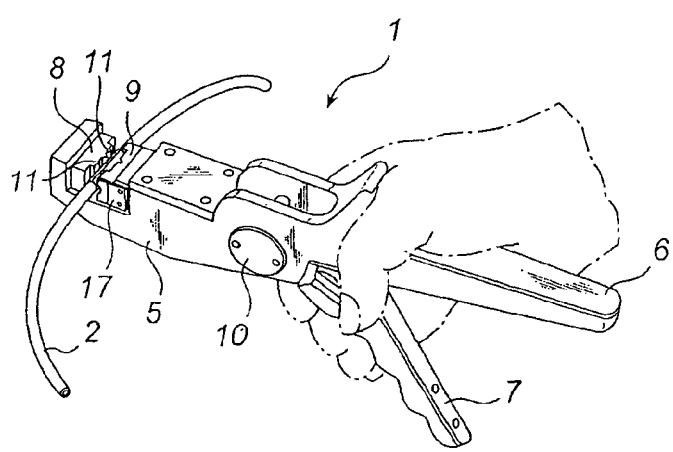
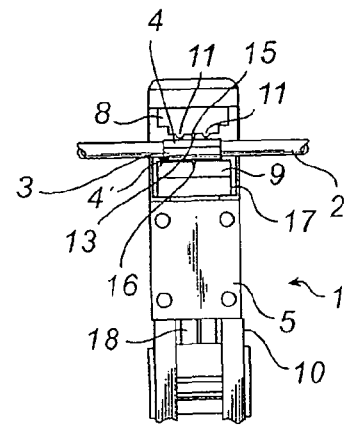
Fig. 2a　　　　Fig. 2b
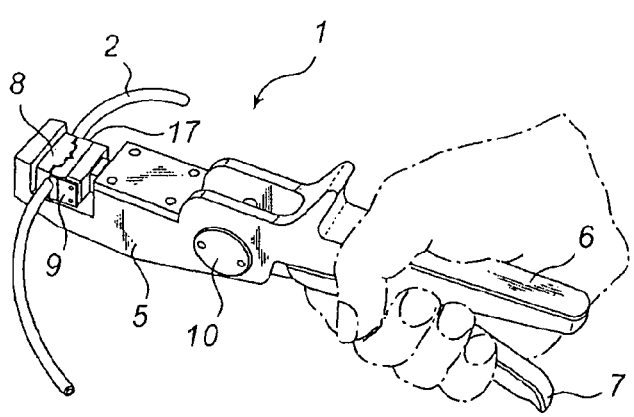
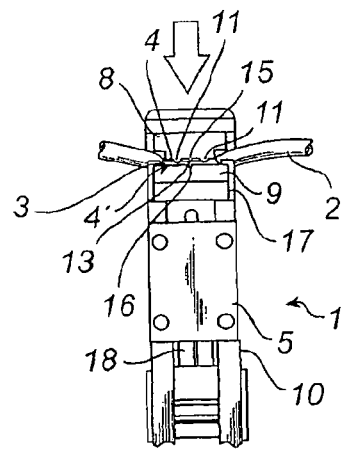
Fig. 3a　　　　Fig. 3b

SEALING MEANS, KIT AND METHOD FOR SEALING OF HOLLOW HOSES OF FLEXIBLE MATERIAL

TECHNICAL FIELD

The present invention relates to a sealing means made of a plastically deformable material for mechanical sealing of hollow hoses of elastic material by means of an appliance having at least two jaws, at least one of which is movable towards and away from the other and which, when moving towards each other, crimp the sealing means against the hose for contamination-tight sealing of the same. The present invention also relates to a kit comprising a sealing means and an appliance for sealing of hollow hoses and to a method for mechanical sealing of hollow hoses.

BACKGROUND OF THE INVENTION

In, for example, devices for introduction and/or withdrawal of a medium in a container there is a need for contamination-free sealing and cutting of the hoses that extend between the conveying means and the collecting vessels which are connected to the process container. The reason for this is that it is desirable that the collecting vessels, after being filled with a medium from the process container, can be moved without any risk of contamination to a laboratory or the like for sampling or analysis of the medium. In the above application, the requirements for good hygienic conditions and contamination-free environment/surroundings are exacting.

Solutions for sealing a hose are previously known in the art, for instance in the form of a folded clip, which is applied to a folded end of the hose. The clip is then crimped against the hose for sealing of the same, whereupon the hose is cut downstream of the clip by means of a pair of scissors or some other cutting tool. However, a solution of this kind does not satisfy the requirements for good hygienic conditions and contamination-free sealing referred to in the application described above. For example the clips do not always provide the desired sealing effect and there is in most cases at least a small portion of the hose left downstream of the clip. There might even be a small portion of the hose left downstream of the clip on both of the cut hose ends. This hose portion or hose portions contain a small quantity of the medium, which may leak out to the surrounding area with an obvious risk of contamination.

Solutions to the above problem have been suggested in, for example, EP 1 090 281, which is owned by the present applicant and which discloses an appliance for sealing a sleeve that has been preassembled around a hose in a contamination-free manner.

A problem associated with this solution, however, is that during storage the material of the preassembled sleeves may crack due to stress corrosion, a consequence of which may be that the desired contamination-free sealing of the hose is not obtained. There is thus a need for a solution that eliminates this problem.

SUMMARY OF THE INVENTION

According to a first aspect of the present invention, the above problem can be eliminated by a sealing means of the kind defined in claim 1. Said sealing means is made of a plastically deformable material for mechanical sealing of hollow hoses of elastic material by means of an appliance having at least two jaws, at least one of which is movable towards and away from the other and which, when moving towards each other, crimp the sealing means against the hose for contamination-tight sealing of the same, wherein the sealing means comprises at least one sealing member, which has two opposite ends and an opening that extends between said ends to allow the at least one sealing member to be slipped onto the hose to be sealed.

Hoses that are to be sealed in a contamination-free manner are often provided with components at their ends, such as a bag for collecting sample liquid or a coupling for connecting the hose to a vessel from which a sample is to be taken. As a rule the components have a size that is greater than the diameter of the hose and because of these components it is therefore often not possible to mount a complete sleeve around the hose afterwards. To obtain a satisfactory contamination-free seal with the kind of sealing means that is crimped against the hose to be sealed, it is also important that the dimension of the sealing means, for example a sleeve, is not too great in proportion to the hose to be sealed. This means that it will be difficult to slip a sleeve with dimensions that are appropriate for satisfactory sealing of the hose onto the hose and move it along the hose, even if the hose has no components at its ends.

Owing to its design, a sealing means as described by way of introduction, which is configured of at least one sealing member, which is provided with a longitudinal opening to allow it to be slipped onto the hose, can be applied around the hose even if the hose is provided with components at its ends. And by applying the at least one sealing member to the hose from the side of the hose, i.e. in a direction transversely of the longitudinal direction of the hose, there is no need to move it along the hose during mounting. This makes it easier for a user to apply the sealing member to the hose and position it at a desired location along the hose.

In other words, the above-described at least one sealing member may be arranged around the hose to be sealed just before sealing is to take place. This means that the sealing means does not have to be applied to the hose in conjunction with the manufacturing of the product, nor does it need to be stored with the hose. As a result the risk of corrosion cracks appearing in the sealing means is reduced. A further advantage is that even if corrosion cracks were to appear in a sealing means, there is no need to discard the whole product, i.e. the hose and its components. Instead another, undamaged sealing means may be applied to the hose.

As mentioned above, a further advantage of the present invention is that the sealing means can be arranged at any optional location along the hose. This distinguishes it from prior art, in which preassembled sleeves were arranged on the hose. The fact that the person who is to seal and cut the hose is able to choose where to dispose the seal is advantageous from the user's point of view.

The at least one sealing member is suitably arranged so as to provide a certain flexibility. This may be achieved, for instance, by selecting an appropriate material and/or appropriate material thickness for the sealing member. Furthermore, it may not be necessary to provide the entire at least one sealing member with flexible characteristics. Instead, it may also be achieved by providing the at least one sealing member with a zone of appropriate material and/or appropriate material thickness. This allows the at least one sealing member to be stretched out when arranging it about the hose and once disposed around the hose it is able to assume its initial shape, which means that a tight fit between the sealing member and the hose can be obtained. Because the at least one sealing member has a certain flexibility, it is also possible to use the same sealing member for hoses of slightly varying diameter.

According to an exemplary embodiment, the sealing means being configured such that a portion of said sealing means overlap a corresponding portion of said sealing means when said sealing means is arranged around the hose to be sealed.

In an embodiment where the sealing means comprises one sealing member with a longitudinal opening extending between its sides, it is the portions of the sealing member that is adjacent the opening, on each side of the opening, that may be provided to overlap each other when the sealing member is arranged around the hose to be sealed.

In an embodiment where the sealing means comprises at least two sealing members, the sealing means may be configured such that a portion of one sealing member, adjacent the opening of that sealing member, may overlap a corresponding portion of another sealing member, wherein the corresponding portion is adjacent the opening of that sealing member.

By arranging the sealing means with an overlap, a sealing means is provided which is applied to the hose in an appropriately tight manner and which, thus, enables a contamination-free sealing thereof. Furthermore, by providing the sealing means in an overlapping manner, it is ensured that the sealing means cover the entire circumference of the hose, which is beneficial when attempting to obtain a contamination-free sealing of the hose.

As mentioned above, because of the certain flexibility of the at least one sealing member, it is also possible to use the same sealing member for hoses of slightly varying diameter. This feature is further enhanced by the fact that the sealing members are adapted to be arranged with a certain overlap relative to each other. The length of the overlap may vary slightly, which too facilitates the use of the same sealing means for hoses of slightly varying size.

According to an exemplary embodiment, said sealing member being adapted such that the portion of the sealing member that border the opening of said sealing member overlap the corresponding portion that border said opening when the sealing member is arranged around the hose to be sealed.

In this embodiment, a sealing means consisting of one sealing member is used. The sealing member is preferably provided with a flexibility that makes it possible to stretch out the opening of the sealing member, in a radial direction of the sealing member. This flexibility makes it possible to arrange the sealing member at the hose to be sealed. Once the sealing member is provided around the hose, the portions adjacent the opening may be provided so that they overlap each other.

According to an exemplary embodiment, a surface extending between a first side and a second side of said opening of said sealing member spans 361-390° of a circle circumscribing said sealing member when said sealing member is arranged around the hose to be sealed, and more preferably spans 370-390° of a circle circumscribing said sealing member when said sealing member is arranged around the hose to be sealed.

The above-mentioned ranges has proven to be beneficial in terms of providing a sufficient overlap of the portions of the sealing member that is provided adjacent the opening of the sealing member. As mentioned above, by making the sealing member somewhat flexible makes it possible to stretch out the opening in a radial direction when applying it to the hose. Thereafter, the sealing member may be provided in a position with an overlap within the above-mentioned ranges.

According to one exemplary embodiment, the sealing means comprises at least two sealing members, each of which has two opposite ends and an opening that extends between said ends to allow the sealing members to be slipped onto the hose to be sealed, the sealing members being adapted such that the portions of a first sealing member that border the opening of said sealing member overlap corresponding portions of a second sealing member when the sealing members are arranged around the hose to be sealed.

As mentioned above, hoses that are to be sealed in a contamination-free manner are often provided with components at their ends, such as a bag for collecting sample liquid or a coupling for connecting the hose to a vessel from which a sample is to be taken. To obtain a satisfactory contamination-free seal with the kind of sealing means that is crimped against the hose to be sealed, it is also important that the dimension of the sealing means, for example a sleeve, is not too great in proportion to the hose to be sealed.

Owing to its design, a sealing means which is configured with two sealing members, each of which is provided with a longitudinal opening to allow them to be slipped onto the hose and then arranged with an overlap, can be applied around the hose even if the hose is provided with components at its ends. And by applying the sealing members to the hose from the side of the hose, i.e. in a direction transversely of the longitudinal direction of the hose, there is no need to move them along the hose during mounting. This makes it easier for a user to apply the sealing members to the hose and position them at a desired location along the hose. By subsequently arranging the sealing members with an overlap relative to each other, a sealing means is provided which is applied to the hose in an appropriately tight manner and which, thus, enables a contamination-free sealing thereof.

In other words, the above sealing members may be arranged around the hose to be sealed just before sealing is to take place. This means that the sealing members does not have to be applied to the hose in conjunction with the manufacturing of the product, nor does it need to be stored with the hose. As a result the risk of corrosion cracks appearing in the sealing means is reduced. A further advantage is that even if corrosion cracks were to appear in a sealing means, there is no need to discard the whole product, i.e. the hose and its components. Instead other, undamaged sealing members may be applied to the hose.

The sealing members are suitably arranged so as to provide a certain flexibility. This may be achieved, for instance, by selecting an appropriate material and/or appropriate material thickness for the sealing members. This allows a slight deflection of the sealing members when arranging them about the hose and once disposed around the hose they are able to assume their initial shape, which means that a tight fit between the sealing member and the hose can be obtained. Because the sealing members have a certain flexibility, it is also possible to use the same sealing members for hoses of slightly varying diameter. This feature is further enhanced by the fact that the sealing members are adapted to be arranged with a certain overlap relative to each other. The length of the overlap on the respective sides of the sleeves may vary slightly, which too facilitates the use of the same sealing means for hoses of slightly varying size.

According to an alternative embodiment, each sealing member consists of a substantially cylindrical element with opposite ends and with an opening that extends between said ends to allow application to the hose.

The above sealing members can be described as having the shape of a cylinder segment. By this is meant that they have the shape of a cylinder with part of the cylindrical surface having been cut away so that a segment of the cylinder remains, i.e. the opening mentioned above extends from one short side of the cylinder along the cylindrical surface to the other end of the cylinder. The two sealing members in the form of cylinder segments together span more than 360 degrees, so that when they are arranged around the hollow hose to be sealed they are positioned with an overlap between adjacent sealing members.

According to an alternative embodiment, a surface extending between a first side and a second side of said opening of at least one of said sealing member spans 180-350° of a circle circumscribing said sealing member. Thus, in an alternative embodiment in which the sealing member has the shape of a cylinder with an imaginary portion cut away so as to form said opening, it is the remaining portion of the cylindrical surface that is able to span 180-350°. This means that an imaginary circular arc of the opening spans 10-180°. In other alternative embodiments, the sealing members may have other shapes than parts of cylinders, in which case the above-stated sizes of respectively the opening and the surface extending between the openings are to be understood as if the sealing member were inscribed in a circle.

According to an alternative embodiment, said surface extending between a first side and a second side of said opening of at least one of said sealing members spans 230-270° of a circle circumscribing said sealing members. Thus, in an alternative embodiment in which the sealing member has the shape of a cylinder with an imaginary portion cut away so as to form said opening, it is the remaining portion of the cylindrical surface that is able to span 230-270°. This means that an imaginary circular arc of the opening spans 90-130°. In other alternative embodiments, the sealing members may have other shapes than parts of cylinders, in which case the above-stated sizes of respectively the opening and the surface extending between the openings are to be understood as if the sealing member were inscribed in a circle.

An opening within the ranges stated above has been found to give a sealing member which has a sufficiently large opening for enabling a user to dispose the sealing member around a hose in a simple manner, while at the same time the opening is not so large that the desired overlap is not obtained.

It is not necessary for both sealing members to have openings of the same size, since the desired overlap can be achieved by having one of the sealing members span a greater part of the circumference of the hose than the other sealing member.

According to an alternative embodiment, a surface extending between a first side and a second side of said opening of each of said sealing members spans 181-350° of a circle circumscribing said sealing members. Thus, in an alternative embodiment in which the sealing member has the shape of a cylinder with an imaginary portion cut away so as to form said opening, it is the remaining portion of the cylindrical surface that is able to span 181-350°. This means that an imaginary circular arc of the opening spans 10-179°. In other alternative embodiments, the sealing members may have other shapes than parts of cylinders, in which case the above-stated sizes of respectively the opening and the surface extending between the openings are to be understood as if the sealing member were inscribed in a circle.

According to an alternative embodiment, a surface extending between a first side and a second side of said opening of each of said sealing members spans 230-270° of a circle circumscribing said sealing members.

Thus, in an alternative embodiment in which the sealing member has the shape of a cylinder with an imaginary portion cut away so as to form said opening, it is the remaining portion of the cylindrical surface that is able to span 230-270°. This means that an imaginary circular arc of the opening spans 90-130°. In other alternative embodiments, the sealing members may have other shapes than parts of cylinders, in which case the above-stated sizes of respectively the opening and the surface extending between the openings are to be understood as if the sealing member were inscribed in a circle.

An opening within the ranges stated above has been found to give a sealing member which has a sufficiently large opening for enabling a user to dispose the sealing member around a hose in a simple manner, while at the same time the opening is not so large that the desired overlap is not obtained. If the sealing members have openings of the same size, the total surface of the sealing members suitably spans more than 360°, so that it is possible to achieve an overlap between the sealing members when they are arranged around a hose.

According to an alternative embodiment, at least one of said sealing members is provided with positioning means for positioning said sealing members at a desired position relative to one another when disposed around the hose to be sealed.

By providing at least one of said sealing members with positioning means which make it easier for a user to arrange the at least two sealing members in the desired position relative to one another, the risk of said at least two sealing members not being positioned with the desired overlap is reduced. The positioning means may be designed in a number of alternative ways and yet provide the desired effect, which is to indicate to a user that the positioning means are positioned with the desired overlap relative to each other. Furthermore, the positioning means may be designed such that they help to lock said at least two sealing members in the desired relative position to prevent them from moving after they have been arranged in the desired position.

According to an alternative embodiment, at least one of said sealing members is provided with a bent portion, the bent portion extending outwards from the surface of the sealing member and being configured such that an edge around the opening of said second sealing member abuts against said bent portion when said first and second sealing members are positioned with the desired overlap around the hose to be sealed.

A positioning means which is designed in this manner will indicate to a user that the sealing members are located in the desired relative positions while contributing to securing or fixing the sealing members in these positions.

According to an alternative embodiment, at least one of said sealing members is provided with a bent portion, the bent portion extending in a direction inwards from the surface of the sealing member and being configured such that an edge around the opening of said second sealing member abuts against said bent portion when said first and second sealing members are positioned with the desired overlap around the hose to be sealed.

According to an alternative embodiment, at least one of said sealing members is provided with slots in the surface of the sealing member, which are arranged such that a portion of the surface of the sealing member has the form of a flap, said flap being bent so as to extend inwards from the surface of the sealing member and being configured such that an edge around the opening of said second sealing member abuts against said bent portion when said first and second sealing members are positioned with the desired overlap around the hose to be sealed.

According to an alternative embodiment, each of said sealing members is provided with positioning means. The positioning means are adapted to cooperate to position and hold the sealing members, so that after they have been brought into the desired overlap around a hose they are maintained in this position.

According to an alternative embodiment, the sealing means are adapted such that said overlap between the sealing members, when arranged around the hose to be sealed, has a length that exceeds the material thickness of said sealing members.

This design offers a sealing means which in use ensures a desired overlap between the sealing members forming the sealing means, which contributes to achieving a satisfactory, contamination-free sealing of a hose when crimping the sealing means. By overlap length is meant its extent from the edge of the opening of one of the sealing members, i.e. its extent in a direction transversely of the longitudinal extension of the sealing member.

According to an alternative embodiment, said sealing members are adapted such that when arranged around said hollow hose they are positioned relative to one another in such a manner that the portions of the first sealing member that border the opening of said sealing member overlap corresponding portions of an adjoining sealing member, the overlap on the respective sides of said opening having a length that exceeds the material thickness of said sealing members.

The sealing members are suitably arranged such that an overlap between the sealing members is achieved on the respective sides of the opening of each of the sealing members. However, the overlap need not be the same on each side of the openings of the sealing members.

When the sealing means is provided with positioning means according to certain exemplifying embodiments, the positioning means may be arranged such that the sealing members are positioned relative to each other in such a manner that the overlap on the respective sides of said opening has a length that exceeds the material thickness of said sealing members. Moreover, the positioning means may be arranged such that the overlap on both sides of the opening of each of the sealing members is substantially the same.

According to a second aspect of the present invention, a kit for mechanical sealing of hollow hoses of elastic material is further provided, the kit comprising a sealing means according to any one of the exemplifying embodiments described above and an appliance having at least two jaws, at least one of which is movable towards and away from the other and which, when moving towards each other, crimp the sealing means against the hose for contamination-tight sealing of the same, wherein at least one of the jaws of the appliance has at least one bar, which projects towards the other jaw and which, when the jaws are moving towards each other, makes an indentation in the sealing means and in the hose to reinforce the sealing thereof as well as the fixing of the sleeve on the hose, and wherein at least one of the jaws has a cutting means, which projects towards the other jaw and which, when the jaws are moving towards each other, makes a cutting indication in the sealing means and in the hose to allow the hose to be cut in a sealing manner.

A set or a kit as described above makes it possible for a user to effect a contamination-free sealing of a hose in such a manner that the problem of preassembled sleeves which may be damaged during storage is eliminated.

According to an exemplifying embodiment of the appliance, the appliance has two straight bars, which are placed substantially in parallel at a distance from each other and extend substantially transversely of the longitudinal direction of the sleeve for making a corresponding number of substantially transverse indentations in the sleeve and in the hose. The transverse indentations may reinforce the sealing thereof as well as the fixing of the sealing members on the hose.

According to an exemplifying embodiment of the appliance, the cutting edge of the appliance extends substantially transversely of the longitudinal direction of the sleeve and makes a substantially transverse cutting indication in the sleeve and in the hose.

According to an exemplifying embodiment of the appliance, the cutting edge of the appliance may be formed as a substantially straight cutting edge, which projects to a greater extent than the bar or bars.

According to an exemplifying embodiment of the appliance, the cutting edge of the appliance cooperates with an opposite recess in the other jaw of the appliance.

According to an exemplifying embodiment of the appliance, the cutting edge is situated substantially halfway between two adjacent bars.

According to an exemplifying embodiment of the appliance, the cutting edge is situated on one side of the bar or bars.

According to an exemplifying embodiment of the appliance, at least one of the jaws has a fixture for fixing the sleeve and the hose between the jaws.

According to an exemplifying embodiment of the appliance, the bar or bars and the cutting edge are arranged on one of the jaws and the fixture on the other jaw, the bar or bars, the cutting edge and the fixture being mounted on or made in one piece with the associated jaw.

According to an exemplifying embodiment of the appliance, the jaw provided with the bar or bars and the cutting edge has the form of a die, which is fixedly mounted in the appliance and the jaw provided with the fixture has the form of a punch, which is mounted in a movable manner in the appliance and is actuatable by a driving means.

According to an exemplifying embodiment of the appliance, the appliance has the form of a pair of tongs which is hand-operated and which has one fixed and one movable leg.

According to an exemplifying embodiment of the appliance, the movable leg actuates, via a gear mechanism forming the driving means, preferably an eccentric mechanism or the like, the jaw forming the punch.

According to an exemplifying embodiment of the appliance, the appliance may be provided with positioning means, which contribute to arranging the sealing means in a desired position in the appliance. This may be advantageous since it may make it easier for a user to make indentations and/or a cut in the sealing members at a desired position.

According to an exemplifying embodiment, the length of the sealing means may be adapted to facilitate the desired sealing, i.e. the sealing means may have a length such that it is easy for a user to position it in the appliance in such a manner that the bars of the appliance and the cutting edge make contact with the sealing means.

According to a third aspect of the invention, a method for mechanical sealing of hollow hoses by means of an appliance having at least two jaws, at least one of which is movable towards and away from each other, is provided. The method comprising the steps of providing a sealing means made of a plastically deformable material, the sealing means comprising at least one sealing member, which has two opposite ends and an opening that extends between said ends;

arranging the sealing means on the hose to be sealed in such a manner that a portion of the sealing means overlap a corresponding portion of the sealing means;

crimping the sealing means against the hose by means of said appliance for contamination-tight sealing.

As mentioned above, hoses that are to be sealed in a contamination-free manner are often provided with components at their ends, such as a bag for collecting sample liquid or a coupling for connecting the hose to a vessel from which a sample is to be taken. As a rule the components have a size that is greater than the diameter of the hose and because of these components it is therefore often not possible to mount a complete sleeve around the hose afterwards. To obtain a satisfactory, contamination-free seal with the kind of sealing means that is crimped against the hose to be sealed, it is also important that the dimension of the sealing means, for example a sleeve, is not too great in proportion to the hose to be sealed. This means that it will be difficult to slip a sleeve with dimensions that are appropriate for satisfactory sealing of the hose onto the hose and move it along the hose, even if the hose has no components at its ends.

Nevertheless, it is possible to apply a sealing means comprising at least one sealing member which comprises a longitudinal opening, to the hose and subsequently arrange it in an overlapping manner, even if the hose has components at its ends. And by applying the sealing means to the hose from the side of the hose, i.e. in a direction transversely of the longitudinal direction of the hose, there is no need to move it along the hose during mounting. This makes it possible for a user to apply the sealing means to the hose and position it at a desired location along the hose. By subsequently arranging the sealing member with an overlap, a sealing means is provided which is applied to the hose in an appropriately tight manner and which, thus, enables a contamination-free sealing thereof. Hence, it is possible to carry out the steps of the above method in rapid succession, i.e. the sealing means does not have to be arranged on the hose or, possibly, stored with the hose a long time before being crimped against the hose. As a result the risk of corrosion cracks appearing in the sealing means is reduced. A further advantage is that even if corrosion cracks were to appear in a sealing means, there is no need to discard the whole product, i.e. the hose and its components. Instead another, undamaged sealing means may be applied to the hose.

In an embodiment where the sealing means comprises one sealing member with a longitudinal opening extending between its sides, it is the portions of the sealing member that is adjacent the opening, on each side of the opening, that may be provided to overlap each other when the sealing member is arranged around the hose to be sealed.

According to an exemplary embodiment, said method for mechanical sealing of hollow hoses further comprises
providing a sealing means comprising two sealing members, each of which has two opposite ends and an opening that extend between said ends,
arranging the respective sealing members on the hose to be sealed,
positioning the sealing members around the hose such that the portions of a first sealing member that border said opening overlap the respective corresponding portions of a second sealing member.

In an embodiment where the sealing means comprises two sealing members, they may be arranged around the hose in such a manner that portions of one of the sealing members, adjacent the opening of that sealing member, overlap corresponding portions of the other sealing member, i.e. portions adjacent the opening of that sealing member.

According to an exemplifying embodiment, the positioning of said sealing members comprises positioning the sealing members such that an edge of one of said sealing members overlaps an edge of an adjacent sealing member with a length that exceeds the material thickness of said sealing members.

According to an exemplifying embodiment in which the sealing means comprises one sealing member, the positioning of said sealing member comprises positioning said sealing member such that an overlap spans 1-30° of an imaginary circle circumscribing said hose, and more preferably spans 10-30° of an imaginary circle circumscribing said hose.

It has been found to be advantageous to position the sealing member or sealing members with an overlap as described above, since this offers a satisfactory, contamination-free sealing of the hose.

According to an exemplifying embodiment, said method for mechanical sealing of hollow hoses according to the above comprises the use of a sealing means as described above.

The method may further comprise providing an appliance for sealing of the hollow hose, which appliance comprises two jaws, at least one of the jaws being movable towards and away from the other jaw and at least one of the jaws having a bar which extends along a straight line and which has an end that projects towards the other jaw. Furthermore, one of the jaws of the appliance may be provided with a cutting means in the form of a substantially straight cutting edge, which projects to a greater extent than said at least one bar. The method may further comprise placing the hose, with the sealing means disposed thereon, between the two jaws. When an appliance as described above is used in the method this results in an indentation in the sealing means and the hose, which forces the sealing means against the hose for sealing of the same, while at the same time a fracture indication is provided in the sealing means and in the hose.

According to an exemplifying embodiment, said method for mechanical sealing of hollow hoses comprises the use of an appliance as described above with respect to a second aspect of the invention and a sealing means as described above with respect to a first aspect of the invention.

BRIEF DESCRIPTION OF THE DRAWINGS

The present invention will be described in more detail below for the purpose of exemplification and with reference to the appended drawings, in which:

FIGS. 2a-2b show, in perspective and from above, respectively, a hose with sealing means which is disposed in a crimping appliance;

FIGS. 3a-3b show, in perspective and from above, respectively, a hose with sealing means which is disposed in an appliance at the final stage of sealing;

DESCRIPTION OF EXEMPLIFYING EMBODIMENTS

Figure 1A:
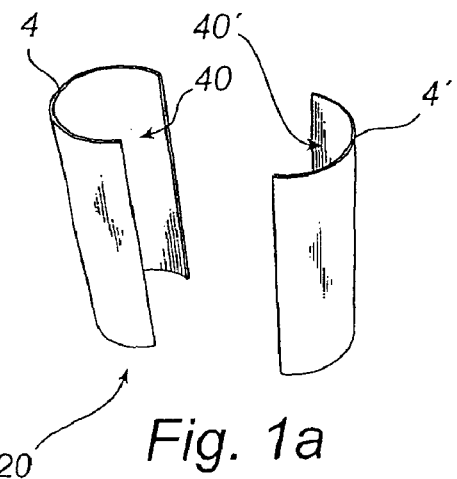
FIGS. 1a-1d illustrate schematically a sealing means according to the invention and how this can be arranged around a hose to be sealed.

FIG. 1a illustrates an exemplifying embodiment of the present invention in the form of a sealing means 20 consisting of two sealing members 4, 4', which in this embodiment have the form of two cylindrical sleeves. The sealing means 20 is intended, for instance, for mechanical sealing, in a contamination-free manner, of the hoses that extend between, for example, process containers and the conveying means and collecting vessels which are connected thereto, so that the latter, after being filled with a medium from the process container, can be moved without any risk of contamination to a laboratory or the like for sampling or analysis of the medium. The sealing means may, of course, also be used in a number of other applications where the requirements for good hygienic conditions and/or contamination-free surroundings and/or working environment are more or less exacting.

The sleeves 4, 4' each have an opening 40, 40', which extends between the short sides of each sleeve. As can be seen in FIG. 1*a*, the sleeves 4, 4' are configured such that their joint cylindrical surface covers a portion that spans more than 360°, i.e. they do not consist of a single cylinder which has been split, but of two separate, original cylinders, which each have had a portion cut away in order to form the opening.

The sleeves 4, 4' need not have the same shape, which means that it is conceivable, for instance, that the cylindrical surface of the sleeve 4 should have a greater extent than the cylindrical surface of the sleeve 4', as seen in the circumferential direction of the sleeves. It is important, however, that they together have an extent in the circumferential direction such that, when disposed around a hose to be sealed, they together span more than 360° in order to overlap each other.

Figure 1B:
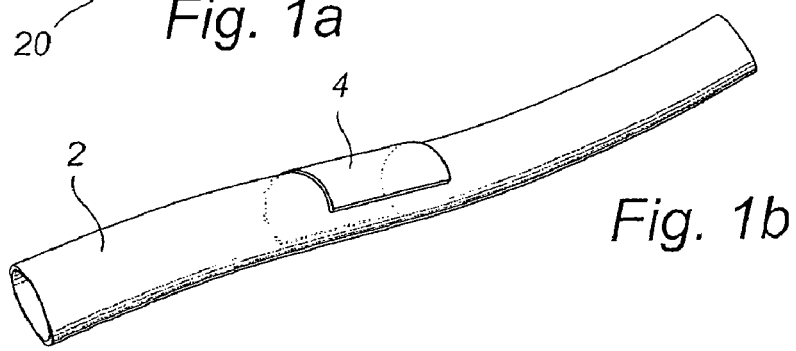
Figure 1C:
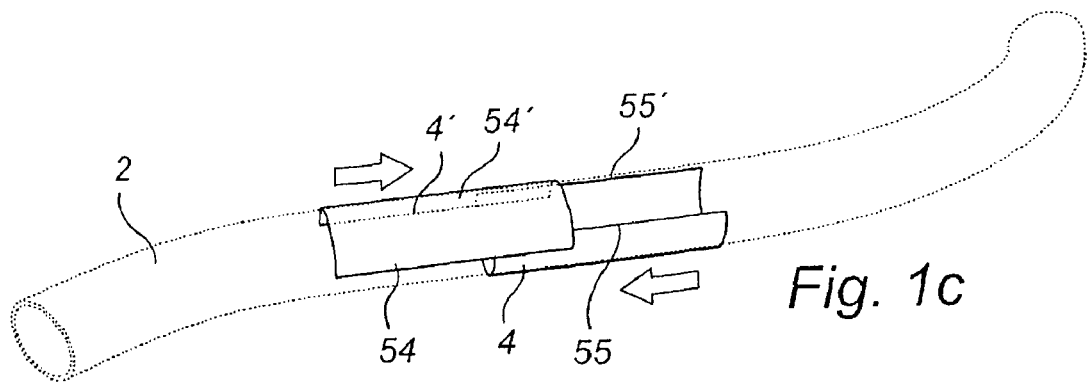
Figure 1D:
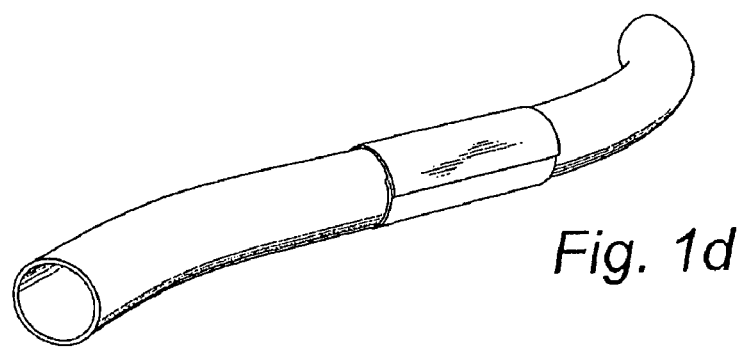

With reference to FIGS. 1*b*-1*d*, the sealing means 20 will be described below when used for sealing of a hollow hose of elastic material, for example rubber or plastic of the appropriate quality.

Figure 4:
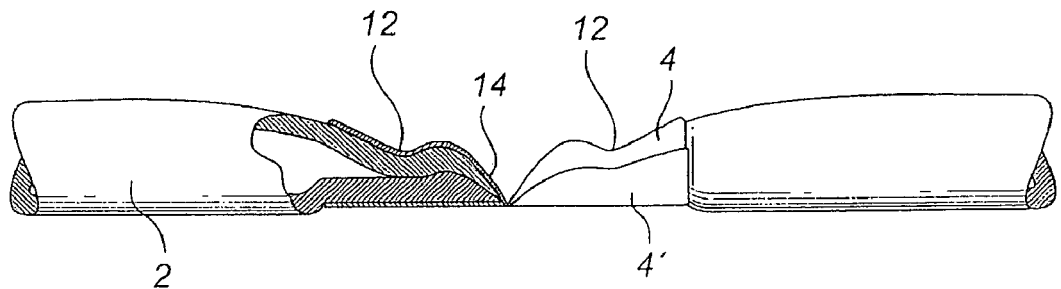
FIG. 4 is a side view of the sealed hose, partly cut-away, in a state after sealing.

FIG. 1*b* shows a hose 2 where a sleeve 4 has been disposed around a part of the circumference of the hose. The hose may be, for instance, a hose that extends between a process vessel (not shown) and a collecting vessel (not shown). FIG. 1*c* illustrates how a second sleeve 4' is applied to the hose. The sleeve 4' is applied to a side of the hose located opposite the side on which the sleeve 4 has been applied. The sleeves 4, 4' are then moved to the position shown in FIG. 1*d*, i.e. opposite one another and, thus, surrounding the hose. As can be seen in FIG. 1*d*, the sleeves 4, 4' overlap. This overlap is provided on both sides of the openings 40, 40' of the sleeves, as is best seen in FIG. 1*c*. By this is meant that the portion 54 that border the opening 40' of the sleeve 4' overlaps with the portion 55 of the sleeve 4 and the portion 54' of the sleeve 4', which is located opposite the portion 54, overlaps with the portion 55' of the sleeve 4. After the sleeves 4, 4' have been applied to the hose 2 as described above, they may be crimped against the hose for sealing of the same. One example of the hose and the sleeves 4, 4' after crimping is shown in FIG. 4.

The overlap between the sleeves 4, 4' may vary. Yet to obtain a satisfactory sealing of the hollow hose 2 they should overlap each other by a length that is not less than the material thickness of the sleeves. This means that the distance with which the portion 54 overlaps the portion 55 should be at least equal to the material thickness of the sleeves 4, 4', which is true also for the distance with which the portion 54' overlaps the portion 55'. The sleeves should not overlap each other in such a manner that there is a layer, somewhere along the sleeve, where the sleeves overlap more than once.

Figures 5A, 5B:
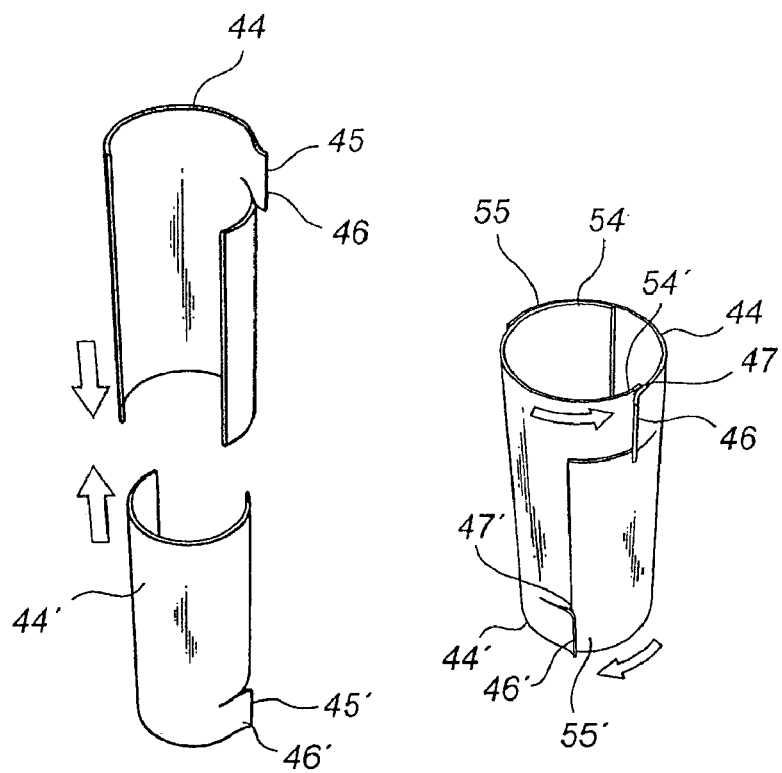
FIGS. 5a-5b show an alternative embodiment of two sealing members which form a sealing means, the sealing members being provided with positioning means.

An alternative embodiment of the sleeves of the sealing means 20 is shown in FIGS. 5*a* and 5*b*, which illustrate two sleeves 44, 44'. The sleeves 44, 44' are designed in substantially the same way as the sleeves 4, 4', but have been provided with positioning means 45, 45', which makes it easier for the user to position the sleeves with the desired overlap around a hose 2. In this embodiment, the positioning means have the form of two portions 46, 46', which extend slightly outwards from the cylindrical surface of the respective sleeves 44, 44'. These portions 46, 46' have been created by cutting the cylindrical surfaces of the respective sleeves and then bending the portions 46, 46' so that they extend outwards at an angle to the cylindrical surfaces. In the application shown in FIG. 5*b*, this allows an edge portion 47, 47' of the other, opposite sleeve to be brought into abutment against said bent portion. When an edge portion 47, 47' is brought into abutment against the bent edge 46, 46', the sleeves can no longer be moved towards each other any further and this serves as an indication to the user that the sleeves are accurately positioned around the hose 2 (not shown in FIG. 5*b*), i.e. that the sleeves are positioned with a desired overlap between the edge portions 54, 54', 55, 55' of the respective sleeves.

Figure 6A:
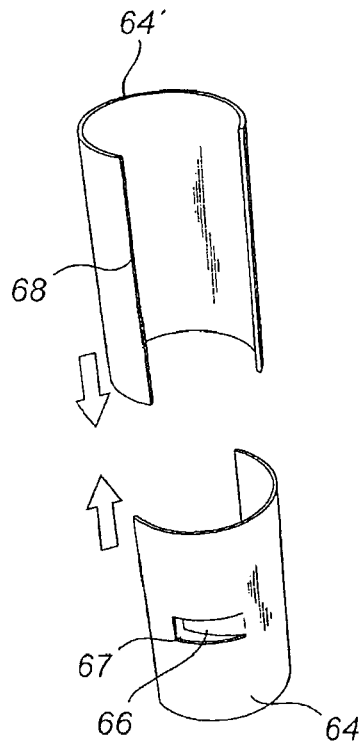
FIGS. 6a-6c show an alternative embodiment of two sealing members which form a sealing means, the sealing members being provided with positioning means according to an alternative embodiment.
Figure 6B:
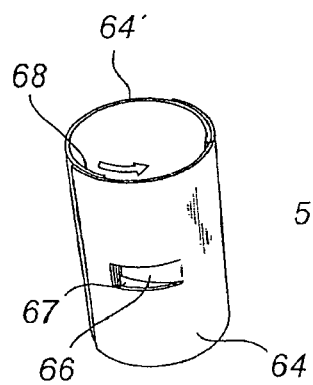
Figure 6C:
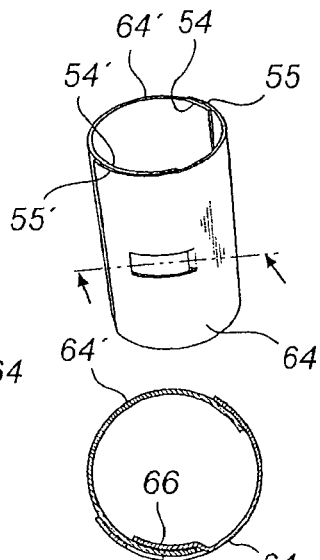

A further alternative embodiment of the sleeves of the sealing means 20 is shown in FIGS. 6*a*-6*c*, which illustrate two sleeves 64, 64'. The sleeves 64, 64' are designed in substantially the same way as the sleeves 4, 4', 44, 44', but have been provided with an alternative embodiment of the positioning means, which makes it easier for the user to position the sleeves with the desired overlap around a hose 2. In this embodiment, the positioning means are in the form of a portion 66, which extends like a flap slightly inwards from the cylindrical surface of one of the sleeves 64. The portion 66 has been created by cutting slots 67 in the cylindrical surface of said sleeve and then bending the portion 66 so that it extends inwards at an angle to the cylindrical surface. In the application shown in perspective in FIG. 6*b* and in cross-section in FIG. 6*c*, this allows a portion of the edge 68 of the other, opposite sleeve 64' to be brought into abutment against said bent portion. When an edge portion 68 is brought into abutment against the bent edge 66, the sleeves can no longer be moved towards each other any further and this serves as an indication to the user that the sleeves are accurately positioned around the hose 2 (not shown in FIGS. 6*b* and 6*c*), i.e. that the sleeves are positioned with a desired overlap between the edge portions 54, 54', 55, 55' of the respective sleeves. In addition, the cooperation between the portion 66 and the edge portion 68 contribute to fixing the sleeves in the desired relative positions once they have been positioned around a hose to be sealed. In the embodiment shown, only the sleeve 64 is provided with a positioning means 66, but it is possible to provide both sleeves 64, 64' with positioning means 66, so that an edge portion of both sleeves, when accurately positioned, is brought into abutment against a portion of the other sleeve.

Figure 7A:
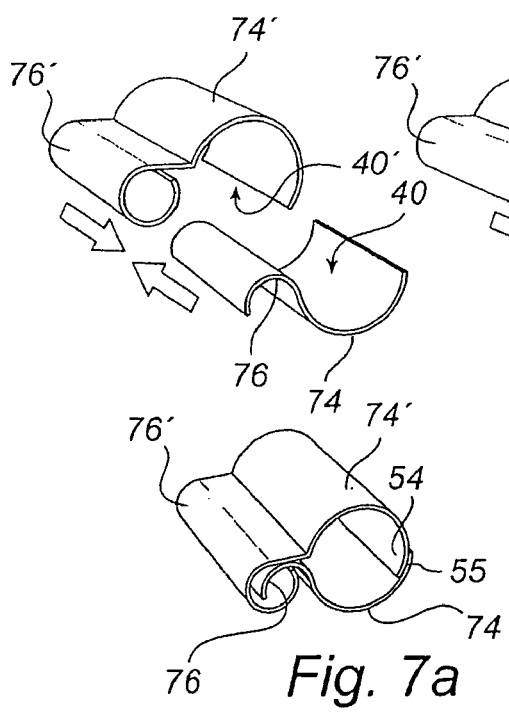
FIGS. 7a-7b show an alternative embodiment of two sealing members which form a sealing means, the sealing members being provided with positioning means according to a further alternative embodiment.
Figure 7B:
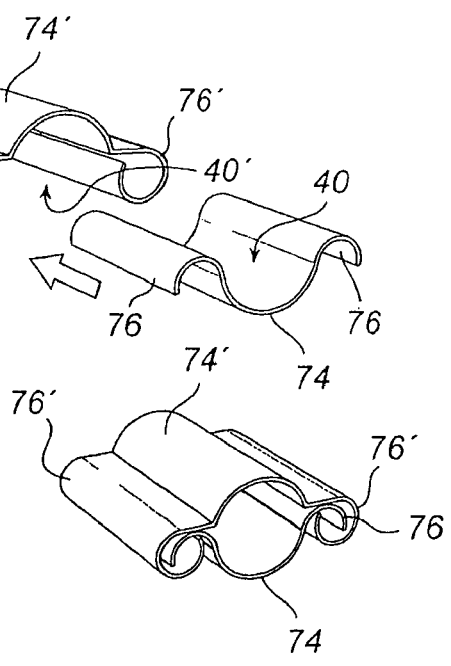

A further alternative embodiment of the sleeves of the sealing means 20 is shown in FIGS. 7*a* and 7*b*, which illustrate two sleeves 74, 74'. The sleeves 74, 74' are designed in substantially the same way as the sleeves 4, 4', 44, 44', 64, 64', but have been provided with an alternative embodiment of the positioning means, which makes it easier for the user to position the sleeves with the desired overlap around a hose 2. In the embodiment shown in FIG. 7*a*, the positioning means are in the form of a portion 76 of a first sleeve and a portion 76' of a second sleeve. These two portions are shaped such that the portion 76 can be inserted in the portion 76', thereby overlapping the latter. The two portions 76, 76' have been formed from the material of the respective sleeves not intended to be in contact with the hose to be sealed by bending it in the desired manner. Thus, the portions 76, 76' are arranged at an edge portion of the cylindrical surface of the respective sleeves 74, 74' in the vicinity of the longitudinal opening of the sleeve and radially outside the cylindrical surface of the sleeve.

In use one of the sleeves is suitably arranged around the hose to be sealed and the other sleeve is then moved along the hose until the sleeves are located opposite each other with the portions 76, 76' engaging each other, as shown in the bottom illustration of FIG. 7a. Owing to the design of the portions 76, 76', the positioning means of the two sleeves are arranged in mutually overlapping manner and so are the portions 54, 55 of the two sleeves when the two positioning means 76, 76' are brought into engagement with each other. This design of the portions 76, 76' is such that the sleeves can only be separated from each other by moving them apart along the axial extension of the hose and this also contributes to fixing the sleeves in the desired relative positions once they have been positioned around a hose to be sealed.

According to a further alternative embodiment, as shown in FIG. 7b, each sleeve is provided with two positioning means 76, 76'. The two positioning means of a sleeve are arranged at the edge portions of the cylindrical surface of the sleeve, i.e. on a respective side of the longitudinal opening of the sleeve. These sleeves and positioning means have the same general design as the one shown in FIG. 7a.

Figure 8A:
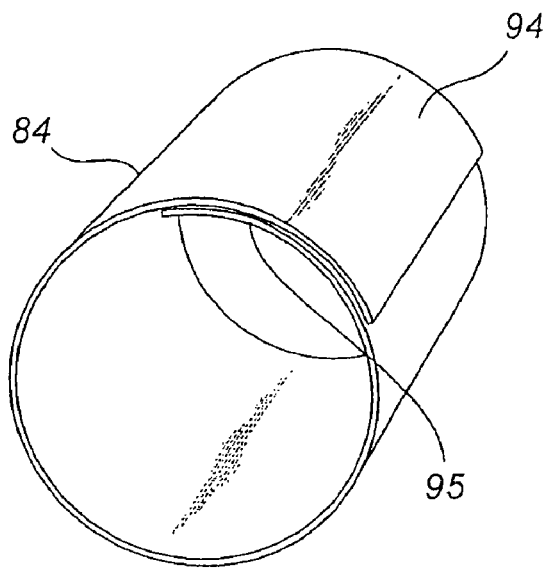
FIGS. 8a-8c show an alternative embodiment of one sealing member that forms a sealing means.
Figure 8B:
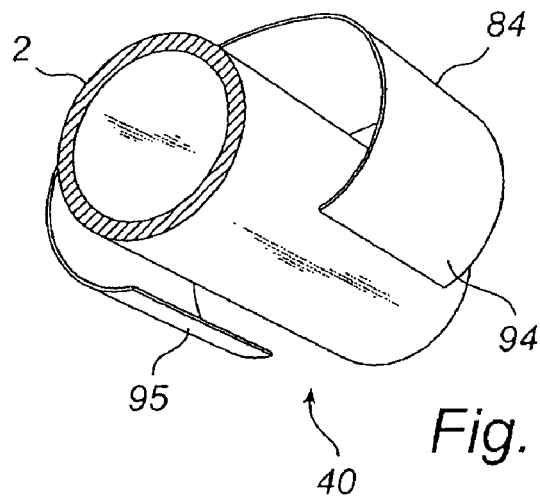
Figure 8C:
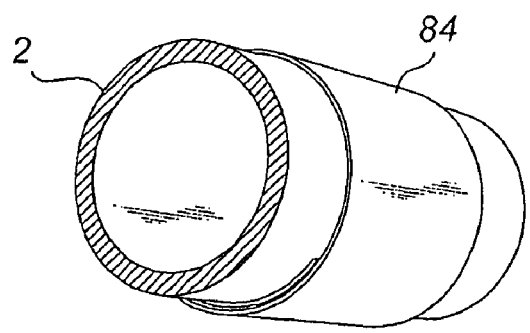

A yet further alternative embodiment of the sealing means 20 is disclosed in FIGS. 8a-8c. In this embodiment, the sealing means 20 consists of one sealing member 84, which has the form of a cylindrical sleeve. The sleeve 84 has an opening 40, which extend between the short sides of the sleeve. As can be seen in FIG. 8a, the sleeve 84 is configured such that its cylindrical surface covers a portion that spans more than 360°, e.g. 361°-390°. Hence, the portions 94, 95 which are provided adjacent the opening 40 overlap each other when the sleeve is in an unaffected condition.

The sleeve 84 is made in an appropriate material that allows the portions 94, 95 adjacent the opening 40 to be bent away from each other, as is shown in FIG. 8b. This allows the sleeve 84 to be positioned around the hose 2 to be sealed. Once the sleeve has been positioned around the hose, the sleeve 84 may return to its unbiased condition in which the portions 94, 95 are overlapping each other.

The dimensions of the sleeves 4, 4'; 44, 44'; 64, 64'; 74, 74'; 84 are dependent on the dimensions of the hose 2 to be sealed. However, owing to a certain inherent flexibility in the sleeves, they need not match the hose size exactly. Instead it is conceivable that the regular radius of the sleeve should be smaller than that of the hose, as long as it is possible to stretch the sleeve to enable application thereof to the hose during use.

The material thickness of the sleeves is dependent on the current application, i.e. the material thickness is adapted to the rigidity of the hose and the strength of the sleeve to ensure that the sleeve is able to withstand the pressure from the hose which it is arranged to seal without being deformed, which might cause it to open. The material thickness may suitably be in the range of 0.25-1 mm. The length of the sleeves is adapted to the coefficient of friction between the hose and the sleeves to prevent the sleeve from falling off when it is crimped against the hose. The length is preferably two or more multiples of the diameter of the hose 2, which in turn, for certain applications, is in the range of 3-40 mm.

The sleeves may suitably be made of an appropriate plastically deformable material, e.g. plastic or metal, having suitable plastic properties. Such metals may be, for instance, brass, titanium, copper, aluminium or alloys thereof.

An appliance for sealing, i.e. crimping of sealing means for hollow hoses according to one aspect of the present invention, is shown in FIGS. 2a-3b. The appliance itself 1 may have form of a hand-operated pair of tongs 5 which has one fixed and one movable leg 6 and 7 and at least two jaws 8 and 9, at least one of which is movable towards and away from the other. When moving the jaws 8, 9 towards each other by manually pressing the legs 6, 7 together and using a driving means 10, which will be described below, the sleeves 4, 4'; 44, 44'; 64, 64'; 74, 74'; 84 are crimped against the hose 2, thereby tightly sealing the same.

More specifically, as best seen in FIG. 2b, at least one of the jaws 8 or 9, in this case the jaw 8, has at least one bar 11 which projects towards the other jaw 9 or 8, in this case the jaw 9. In the above-described movement of the jaws 8, 9 towards each other, this bar 11 makes a marked indentation 12 in the sleeves 4, 4'; 44, 44'; 64, 64'; 74, 74'; 84 and in the hose 2. In the preferred embodiment, there are essentially two such bars 11, which are placed substantially in parallel at a distance from each other and extend substantially transversely of the longitudinal direction of the sleeves 4, 4'; 44, 44'; 64, 64'; 74, 74'; 84. The bars are preferably straight and make two substantially transverse indentations 12 in the sleeves 4, 4'; 44, 44'; 64, 64'; 74, 74'; 84 and in the hose 2 to reinforce the sealing thereof as well as the fixing of the sleeves 4, 4'; 44, 44'; 64, 64'; 74, 74'; 84 on the hose 2. If desired and if suitable, there may, of course, be more than two such bars 11 or bars which are differently placed/formed on said jaw 8.

Moreover, at least one of the jaws 8 or 9, also in this case the jaw 8, has a cutting means 13 projecting towards the other jaw 9 or 8. When the jaws 8, 9 are moving towards each other in the described manner, this cutting means 13 makes a cutting indication 14 in the sleeves 4, 4'; 44, 44'; 64, 64'; 74, 74'; 84 and in the hose 2 to allow the sleeve and the hose to be cut in a sealing manner.

In the embodiment shown, the cutting means 13 is preferably formed as a substantially straight cutting edge 15. The cutting edge extends substantially transversely of the longitudinal direction of the sleeves 4, 4'; 44, 44'; 64, 64'; 74, 74'; 84 and thus makes a substantially trans-verse cutting indication 14 in the sleeves 4, 4'; 44, 44'; 64, 64'; 74, 74'; 84 and in the hose 2. The cutting edge 15 projects to a greater extent than the bars 11 and suitably cooperates with an opposite, straight recess 16 in the opposite jaw, in this case the jaw 9. The depth, width and form of the recess 16 may vary, and the recess is suitably adapted to the form of the cutting edge 15 and to the qualities of the material of the hose 2 and the sleeves 4, 4'; 44, 44'; 64, 64'; 74, 74'; 84. In certain applications, the recess 16 can, if required or desired, be omitted.

Preferably, the cutting edge 15 is situated substantially halfway between the bars 11, if they are two in number. If there are further bars 11, the cutting edge 15 is suitably placed halfway between two adjacent bars, preferably the ones situated closest to the middle. In a certain application, it is, of course, also possible to place the cutting edge 15 outside or on one side of the bar or the bars 11.

The cutting indication 14 mentioned above is preferably such that the sleeves 4, 4'; 44, 44'; 64, 64'; 74, 74'; 84 and the hose 2 are not cut or broken directly when sealing by means of the appliance 1, but at an optional point of time after that. Then the sleeves 4, 4'; 44, 44'; 64, 64'; 74, 74'; 84 and the hose 2 are separated along the cutting indication 14 by manual or mechanical bending back and forth, until the sleeves are divided by fatigue fracture. An example of a crimped but not yet cut hose 2 with sleeves 4, 4'; 44, 44'; 64, 64'; 74, 74'; 84 is shown in FIG. 4.

Naturally, nothing prevents the sleeves 4, 4'; 44, 44'; 64, 64'; 74, 74'; 84 and the hose 2 from being separated along the cutting indication 14 directly in connection with the actual sealing.

To fix the sleeves 4, 4'; 44, 44'; 64, 64'; 74, 74'; 84 and the hose 2 in the intended position between the jaws 8 and 9 in the appliance 1 when sealing, at least one of the jaws 8 or 9, in this case the jaw 9, has a fixture 17. The fixture fixes and supports the hose 2 and the sleeve 4 laterally, horizontally and vertically and can be formed in an optional manner.

For practical and other reasons, in the disclosed and described embodiment the bars 11 and the cutting edge 15 are arranged on one of the jaws 8 or 9, in this case the jaw 8, and the fixture 17 on the other, opposite jaw 9 or 8, in this case the jaw 9. The bars 11, the cutting edge 15 and the fixture 17 can be mounted on the associated jaw with the aid of suitable attachment means, which are not shown. Alternatively, one/ some of or all these components can be made in one piece with the associated jaw. In the shown case, the bars 11 and the cutting edge 15 are made in one piece with the associated jaw, whereas the fixture 17 is mounted on the associated jaw.

In the preferred embodiment, the jaw 8 provided with the bars 11 and the cutting edge 15 suitably has the form of a die, which is fixedly mounted in the appliance 1 with the aid of attachment means (not shown). In a corresponding manner, the jaw 9 provided with the fixture 17 has the form of a punch. This punch is mounted in a slidable manner (not shown) in the appliance 1 and is actuatable by the previously mentioned driving means 10. The driving means 10 suitably consists of a gear mechanism generally designated 18, which can be an eccentric mechanism or the like and which is suitably connected to and actuatable by means of the movable leg 7 of the pair of tongs 5.

The invention is not, of course, limited to the embodiments which are described above and shown in the drawings, and can be modified in many different ways within the scope of protection according to the appended claims.

The sleeves 4, 4'; 44, 44'; 64, 64'; 74, 74'; 84 need not necessarily have the form of substantially cylindrical sleeves, but also other shapes are conceivable. It is possible, for example, to use sleeves which are oval, square, octagonal etc.

The positioning means adapted to ensure a desired overlap between the sleeves need not have the forms described above but may be provided in alternative ways. It is conceivable, for instance, to have other forms of flaps or lugs against which an edge portion of the second sleeve may abut than the ones described above. It is also conceivable to have positioning means of other designs, which are based on the same concept as that shown in FIGS. 7a and 7b.

By varying the diameter and material thickness of the sealing means as well as the design of the appliance that crimps the sealing means, the inventive idea can be used for hoses of varying diameter and material thickness. This is an advantage, since different hoses are used for different applications in which a contamination-free sealing is desirable.

The appliance 1 does not, for example, need to be a manually operable pair of tongs, but it can alternatively be a separate tool or a tool which is included in a machine and driven electrically, pneumatically, hydraulically etc according to need and desire. The jaws 8, 9 with the associated components (bars 11, cutting edge 15 and fixture 17) can be attached to the appliance 1 in a replaceable manner and match the size of the hose 2 and the sleeve 4, 4'; 44, 44'; 64, 64'; 74, 74' and/or be mutually exchangeable.

In another embodiment, the cutting edge can be pivotally affixed to the tool and/or jaw. The tool or jaw and can have a slot in which the cutting edge can be moved so as to be in line with the jaw or extending beyond it so as to perform the cutting function as described above.

The length of the overlap of the sealing members can vary within a relatively large range. Factors that are of importance for determining which overlap is desirable are, for example, that the sealing means must be easy for the user to mount and that they must provide an overlap that is sufficiently large to ensure that a contamination-free seal is obtained. It is possible, for instance, to have the overlap vary between a few degrees of an imaginary circle circumscribing the sealing means and up to twice the material thickness of the hose to be sealed. The material thickness of the hoses in certain types of applications may typically be in the range of 0.5 to 5 mm.

The invention claimed is:

1. A sealing member comprising a plastically deformable material for mechanical sealing of hollow hoses of elastic material in use with an appliance having at least two jaws, at least one of which is movable towards and away from the other and which, when moving towards each other, crimp the sealing member against the hose and cut the hose and the sealing member for contamination-tight sealing of the hose, wherein the sealing member comprises at least two sealing members, each of which has two opposite ends and an opening that extends between said ends to allow the sealing members to be slipped onto the hose to be seated, the sealing members being adapted such that the portions of a in sealing member that border the opening of said sealing member overlap corresponding portions of a second sealing member when the sealing members are arranged around the hose to be sealed and wherein a surface extending between a first side and a second side of said opening of at least one of said sealing members spans 230-270° of a circle circumscribing said sealing members.

2. A sealing member according to claim 1 wherein a portion of at least one of the at least two sealing members that borders one side of the opening of said sealing members overlaps a corresponding portion of the other sealing member on the opposite side of the opening and spans 361-390° of a circle circumscribing said sealing member.

3. A sealing member as claimed in claim 1, wherein each sealing member consists of a substantially cylindrical element with opposite ends and with an opening that extends between said ends to allow application to the hose.

4. A sealing member of claim 1 wherein the at least two sealing members have a surface extending between a first side and a second side of said opening of each of said sealing members spans 230-270° of a circle circumscribing said sealing members.

5. A sealing member of claim 1 wherein at least one of said sealing members is provided with positioning means for positioning said sealing members at a desired position relative to one another when disposed around the hose to be sealed.

6. A sealing member of claim 1 wherein at least one of said sealing members is provided with a bent portion, the bent portion extending outwards from the surface of the sealing member and being configured such that an edge around said opening of said second sealing member abuts against said bent portion when said first and second sealing members are positioned with the desired overlap around the hose to be sealed.

7. A sealing member of claim 1 wherein the sealing members are adapted such that said overlap between the sealing members when disposed around the hose to be sealed, has a length that exceeds the material thickness of said sealing members.

8. A sealing member of claim 1 wherein the overlap on the respective sides of said opening having a length that exceeds the material thickness of said sealing members.

9. The sealing member of claim 1 further comprising the hose having a first and second end, the first end of the hose being attached to a first component and the second end of the hose being attached to a second component and the sealing members being positioned over the hose between it first and second end.

10. A method for mechanical sealing of hollow hoses by means of an appliance having at least two laws, at least one of which is movable towards and away from each other, comprising the steps of
provide a hose having a first and second end, the first end of the hose being attached to a first component, the second end of the hose being attached to a second component,
providing a sealing member made of a plastically deformable material, the sealing member comprising two sealing members, each of which has two opposite ends and an opening that extends between said ends to allow the sealing members to be slipped onto the hose between its first and second end;
arranging the respective sealing members on the hose in such a manner that a portion of one sealing member overlap a corresponding portion of the other sealing member by a length that exceeds the material thickness of said sealing member;
crimping the sealing members against the hose by means of said appliance for contamination-tight sealing and cutting the sealing members and hose.

11. A kit for mechanical sealing of hollow hoses of elastic material, the kit comprising a sealing member formed of a plastically deformable material for mechanical sealing of hollow hoses of elastic material wherein the sealing member is at least two sealing members each in the form of a cylindrical sleeve having a length and which has two opposite ends and an opening that extends the length of the sleeve between said ends to allow the at least two sealing members to be slipped onto the hose to be sealed and an appliance having at least two jaws, at least one of which is movable towards and away from the other and which, when moving towards each other, crimp the sealing members against the hose for contamination-tight sealing of the same, wherein at least one of the jaws of the appliance has at least one bar which projects towards the other jaw and which, when the jaws are moving towards each other, makes an indentation in the sealing members and the hose to reinforce the sealing thereof as well as the fixing of the sealing members on the hose, and wherein at least one of the jaws has a cutting means, which projects towards the other jaw and which, when the jaws are moving towards each other, makes a cutting indication in the sealing members and the hose to allow the hose to be cut in a sealing manner.

12. The kit of claim 11 further comprising the hose having a first and second end, the first end of the hose being attached to a first component and the second end of the hose being attached to a second component and the sealing members being positioned over the hose between its first and second end.

* * * * *